US006251669B1

(12) United States Patent
Luskin

(10) Patent No.: US 6,251,669 B1
(45) Date of Patent: *Jun. 26, 2001

(54) NEURONAL PROGENITOR CELLS AND USES THEREOF

(75) Inventor: Marla B. Luskin, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/003,006

(22) Filed: Jan. 5, 1998

Related U.S. Application Data

(63) Continuation of application No. 08/499,093, filed on Jul. 6, 1995, now Pat. No. 5,753,505.

(51) Int. Cl.⁷ .............................. C12N 5/00; C12N 5/02; C12Q 1/68; C12P 21/06; A61K 48/00
(52) U.S. Cl. ........................... 435/375; 435/6; 435/69.1; 424/93.21
(58) Field of Search .................................. 435/375, 368, 435/325, 354, 377

(56) References Cited

U.S. PATENT DOCUMENTS

| 5,082,670 | 1/1992 | Gage et al. | 424/520 |
|---|---|---|---|
| 5,175,103 | 12/1992 | Lee | 435/455 |
| 5,589,376 | 12/1996 | Anderson et al. | 435/325 |

FOREIGN PATENT DOCUMENTS

| WO 90/06757 | 6/1990 | (WO) . |
|---|---|---|
| WO 93/10234 | 5/1993 | (WO) . |
| WO 94/16059 | 7/1994 | (WO) . |

OTHER PUBLICATIONS

Price et al. "Cell lineage in the rat crebral cortex: a study using retroviral–mediated gene transfer," Development, vol. 104: 473–482, 1988.*
Davis et al. "A self–renewing multipotential stem cell in embryonic rat cerebral cortex," Nature, vol. 372: 263–266, Nov. 17, 1994.*
Ray, et al. "Proliferation, differentiation, and long–term culture of primary hippocampal neurons" Proc. Natl. Acad. of Sci. of USA, 90(8):3602–3606, Apr. 1993.
Carnahan & Patterson "Isolation of the progenitor cells of the sympathoadrenal lineage from embryonic sympathetic ganglia with the SA monoclonal antibodies" J. Neuroscience 11(11):3520–30, 1991.
Luskin, M.B., "Restricted Proliferation and Migration of Postnatally Generated Neurons Derived from the Forebrain Subventricular Zone" *Neuron* 11:173 (1993).
Reynolds & Weiss, "Generation of Neurons and Astrocytes from Isolated Cells of the Adult Mammalian Central Nervous System" *Science* 255:1707 (1992).
Cattaneo & McKay, "Proliferation and Differentiation of Neuronal Stem Cells Regulated by Nerve Growth Factor" *Nature* 347:762 (1990).

Frederiksen & McKay, "Proliferation and Differentiation of Rat Neuroepithelial Precursor Cells in Vivo" *J. Neurosci.* 8:1144 (1988).
Kirschenbaum et al., "In Vitro Neuronal Production and Differentiation by Precursors Cells Derived from the Adult Human Forebrain" *Cerebral Cortex* 4:576 (1994).
Kirschenbaum & Goldman, "Brain–Derived Neurotrophic Factor Promotes the Survival of Neurons Arising from the Adult Rat Forebrain Subependymal Zone" *Proc. Natl. Acad. Sci.*, 92:210 (1995).
Lois & Alvarez–Buylia, "Proliferating Subventricular Zone Cells in the Adult Mammalian Forebrain can Differentiate into Neurons and Glia" *Proc. Natl. Acad. Sci. U.S.A.* 90:2074 (1993).
Gage et al., "Isolation, Characterization, and use of Stem Cells from the CNS" *Annu. Rev. Neurosci.* 18:159 (1995).
Vaysse & Goldman, "A Clonal Analysis of Glial Lineages in Neonatal Forebrain Development in Vitro" *Neuron* 5:227 (1990).
Lubetzki et al., "Clonal Segregation of Oligodendrocytes and Astrocytes During in Vitro Differentiation of Glial Progenitor Cells" *Glia* 6:289 (1992).
Kilpatrick & Bartlett, "Cloning and Growth of Multipotential Neural Precursors: Requirements for Proliferation and Differentiation" *Neuron* 10:255 (1993).
Morshead et al., "Neural Stem Cells in the Adult Mammalian Forebrain: A Relatively Quiescent Subpopulation of Subependymal Cells" *Neuron* 13:1071 (1994).
Reynolds et al., "A Multipotent EGF–Responsive Striatal Embryonic Progenitor Cell Produces Neurons and Astrocytes" *J. Neuroscience* 12:4565 (1992).
Temple, S., "Division and Differentiation of Isolated CNS Blast Cells in Microculture" *Nature* 340:471 (1989).
Vescovi et al., "bFGF Regulates the Proliferative Fate of Unipotent (Neuronal) and Bipotent (Neuronal/Astroglial) EGF–Generated CNS Progenitor Cells" *Neuron* 11:951 (1993).
Price, et al., "Cell Lineage in the Rat Cerebral Cortex: A Study Using Retroviral–Mediated Gene Transfer" *Development* 104:473–482 (1988).
Davis, et al., "A Self–Renewing Multipotential Stem Cell in Embryonic Rat Cerebral Cortex" *Nature* 372:263–266 (1994).
Gritti, et al., "Multipotential Stem Cells from the Adult Mouse Brain Proliferate and Self–Renew in Response to Basic Fibroblast Growth Factor" *J. of Neuroscience* 16(3):1091–1100 (1996).

* cited by examiner

Primary Examiner—Karen M. Hauda
Assistant Examiner—Joseph T. Woitach
(74) Attorney, Agent, or Firm—Needle & Rosenberg, P.C.

(57) ABSTRACT

The present invention provides an isolated cellular composition comprising greater than about 90% mammalian, non tumor-derived, neuronal progenitor cells which express a neuron-specific marker and which can give rise to progeny which can differentiate into neuronal cells. Also provided are methods of treating neuronal disorders utilizing this cellular composition.

16 Claims, 2 Drawing Sheets

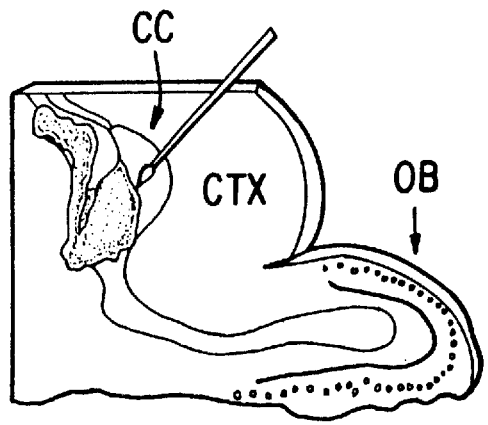
DISSECTION
FIG.1A
DISSOCIATION
FIG.1B
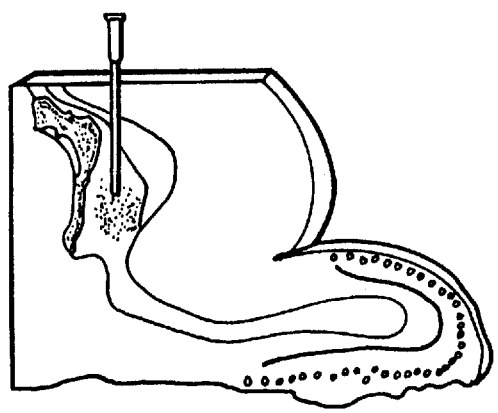
LABELING
FIG.1C
TRANSPLANTATION
FIG.1D

DISSECTION

DISSOCIATION

LABELING

TRANSPLANTATION

NEURONAL PROGENITOR CELLS AND USES THEREOF

This application is a continuation of, and claims the benefit of, application Ser. No. 08/499,093, filed Jul. 6, 1995 now U.S. Pat. No. 5,753,505.

This invention was made with government support under NIH grant number NS 28380 awarded by the National Institutes of Health. The government has certain rights in the invention.

BACKGROUND OF THE INVENTION

1. Field of the Invention

The present invention relates to an isolated cellular composition comprising a substantially homogeneous population of mammalian neuronal progenitor cells. Additionally, the present invention relates to methods of delivering biologically active molecules to a mammalian brain by transplanting the cellular composition to the brain.

2. Background Art

Because mammalian neurons are generally incapable of dividing when mature, sources of dividing neuronal cells have been sought. Several difficulties have arisen, however, in identifying sources of dividing cells that generate neurons because neuronal progenitor cells frequently fail to express neuronal markers and because heterogeneous populations of cells (including neuronal and non-neuronal cells) generally arise.

Neoplastic cell lines and immortalized neuronal precursors have been used to provide relatively homogeneous populations of cells. Because these cells are rapidly dividing, they generally show a limited ability to fully differentiate into cells with a neuronal phenotype. For example, PC12 cells derived from a pheochromocytoma fail to differentiate or maintain a differentiated state in culture in the absence of nerve growth factor (NGF). (Green and Tischler, *Advances in Cellular Neurobiology*, S. Federoff and L. Hertz, eds. (Academic Press, N.Y.), (1982). Additionally, these cells are tumor-derived and have neoplastic characteristics.

Similarly, embryonal carcinoma cell lines have been differentiated in culture under special conditions. NT2 cells, derived from a teratocarcinoma, will differentiate in culture only following extended treatment with retinoic acid. The NT2 cells, however, differentiate into both neuronal and non-neuronal cell types. The resulting mixed culture must be treated with mitotic inhibitors and then the cells replated to remove the dividing non-neuronal cells and approach a relatively pure population of neuronal cells. (U.S. Pat. No. 5,175,103). These relatively pure neuronal cells nonetheless are tumor-derived and have neoplastic characteristics.

Sources of neuronal precursors from adult and neonatal mammalian nervous systems have generally resulted in similar problems with heterogeneity. Reynolds and Weiss, *Science* 255:1707 (1992), have cultured cells from the adult striatum, presumably including portions of the subventricular zone. The cells were cultured in the presence of epidermal growth factor (EGF) and allowed to form large cell clusters, which were termed "neurospheres." The spheres were then dissociated and the cells were cultured in the presence of EGF. The resulting cell cultures consisted of a mixture of post-mitotic neurons, glia, and subependymal cells. Thus, by these means, some of the newly-generated cells were induced to differentiate into neurons; however, the proportion of neurons obtained is low by this method. Others have been able to induce some neuronal proliferation from cultures of the neonatal telencephalon, by administration of fibroblast growth factor. Like the method of Reynolds and Weiss, this neonatal source also results in low proportions of neurons compared to non-neuronal cells. Relatively pure populations of neuronal cells can be achieved by these methods only following treatment with mitotic inhibitors. Therefore, the relatively pure neuronal cells are post-mitotic.

The subventricular zone is known to be a source of certain dividing cells in the nervous system. However, the subventricular zone has been viewed exclusively as a source of glia and not neurons (Paterson et al., *J Comp. Neurol.*, 149:83, 1973; LeVine and Goldman, *J Neurosci*, 8:3992, 1988; Levison and Goldman, *Neuron* 10:201 (1993). This was the consensus concerning the intact, in vivo subventricular zone. Luskin, *Neuron*, 11:173 (1993) found that a discrete region of the intact subventricular zone produced numerous neurons that differentiated into olfactory bulb neurons in vivo. However, investigators who have cultured cells derived from the neonatal subventricular zone have shown that the vast majority of these cells become glia when cultured (Vaysse and Goldman, *Neuron*, 4:833, 1990; Lubetzki et al., *Glia*, 6:289, 1992). Lois and Alvarez-Buylla, *Proc. Natl. Acad Sci.*, 90:2074, (1993) cultured explants of the subventricular zone from adult mammalian forebrain, and found a preponderance of glia.

Thus, a simple means of obtaining a composition of cells having a high percentage of neuronal progenitor cells and a correspondingly low percentage of non-neuronal cells is needed. Such a composition and method for achieving the composition would offer several advantages over prior compositions and methods. Dividing cells can be manipulated through gene transfer. In addition, neuronal cells which differentiate and eventually cease dividing result in a decreased likelihood of tumor formation when transplanted into a host nervous system. Glia, in contrast to neurons, can be highly proliferative when given certain signals and can even form gliomas. Neoplastic cell lines can similarly result in tumor formation.

In contrast to the above-described studies which support that only glia arose from the cultured telencephalic subventricular zone or that only a low fraction of neurons could be obtained under particularly favorable conditions, the present invention provides an isolated cellular composition comprised of a substantially homogeneous population of mammalian, non tumor-derived neuronal progenitor cells which express a neuron-specific marker and which can give rise to progeny which can differentiate into neuronal cells. This ability of these cells to divide is atypical because most cells expressing neuron-specific cell markers are post-mitotic cells. Also, the present composition comprises a population of cells of such homogeneity that greater than about 90% of the neuronal progenitor cells express a neuron-specific marker and can give rise to progeny which can differentiate into neuronal cells.

SUMMARY OF THE INVENTION

The present invention provides an isolated cellular composition comprising greater than about 90% mammalian, non tumor-derived, neuronal progenitor cells which express a neuron-specific marker and which can give rise to progeny which can differentiate into neuronal cells.

The instant invention additionally provides a method of delivering a biologically active molecule produced by the neuronal progenitor cells, or their progeny, or mixtures thereof, of a cellular composition comprising greater than about 90% mammalian, non tumor-derived, neuronal progenitor cells which express a neuron-specific marker and which can give rise to progeny which can differentiate into neuronal cells to a region of a mammalian brain, comprising transplanting the cellular composition into the region of the brain, thereby delivering a biologically active molecule produced by the cells or their progeny to the region.

Additionally, the present invention provides a method of delivering a biologically active molecule produced by the neuronal progenitor cells, or their progeny, or mixtures thereof, of a cellular composition comprising greater than about 90% mammalian, non tumor-derived, neuronal progenitor cells which express a neuron-specific marker and which can give rise to progeny which can differentiate into neuronal cells and which are transfected with an exogenous nucleic acid that functionally encodes a biologically active molecule to a region of a mammalian brain comprising transplanting the cellular composition into the region of the brain, thereby delivering the biologically active molecule produced by the cells or their progeny to the region.

The present invention further provides a method of treating a neuronal disorder characterized by a reduction of catecholamines in the brain of a mammal, comprising transplanting into the brain a cellular composition comprising greater than about 90% mammalian, non tumor-derived, neuronal progenitor cells which express a neuron-specific marker and which can give rise to progeny which can differentiate into neuronal cells, or their progeny, or mixtures thereof, thereby providing a source of catecholamines to the brain and treating the disorder.

Also provided by the present invention is a method of treating Alzheimer's disease in a subject comprising transplanting into the brain of the subject a cellular composition comprising greater than about 90% mammalian, non tumor-derived, neuronal progenitor cells which express a neuron-specific marker and which can give rise to progeny which can differentiate into neuronal cells and which are transfected with an exogenous nucleic acid that functionally encodes a biologically active molecule that stimulates cell division or differentiation or that functions in the synthesis of a neurotransmitter, or their progeny, or mixtures thereof, thereby treating Alzheimer's disease.

The present invention additionally provides a method of treating a neuronal disorder characterized by a reduction of γ-aminobutyric acid in the brain in a mammal, comprising transplanting into the brain a cellular composition comprising greater than about 90% mammalian, non tumor-derived, neuronal progenitor cells which express a neuron-specific marker and which can give rise to progeny which can differentiate into neuronal cells, or their progeny, or mixtures thereof, thereby providing a source of γ-aminobutyric acid to the brain and treating the disorder.

Also provided by the present invention is a method of screening for a marker of neuronal cells comprising obtaining the neuronal progenitor cells of a cellular composition comprising greater than about 90% mammalian, non tumor-derived, neuronal progenitor cells which express a neuron-specific marker and which can give rise to progeny which can differentiate into neuronal cells, and detecting the presence of a marker in the neuronal progenitor cells that is not present in non-neuronal cells, the marker present in the neuronal progenitor cells that is not present in the non-neuronal cells being a marker of neuronal cells.

The present invention also provides a method of detecting a neuronally expressed gene comprising obtaining a cDNA library from the neuronal progenitor cells of a cellular composition comprising greater than about 90% mammalian, non tumor-derived, neuronal progenitor cells which express a neuron-specific marker and which can give rise to progeny which can differentiate into neuronal cells, obtaining a cDNA library from a non-neuronal cell, determining the presence at higher levels of a cDNA in the library from the neuronal progenitor cells than in the non-neuronal cell, the presence at higher levels of a cDNA in the library from the neuronal progenitor cells indicating a neuronally expressed gene.

The present invention further provides a method of obtaining an isolated cellular composition comprising greater than about 90% mammalian, non tumor-derived, neuronal progenitor cells which express a neuronal marker and which can give rise to progeny which can differentiate into neuronal cells, comprising isolating cells from the portion of a mammalian brain that is the equivalent of the anterior portion of the subventricular zone at the dorsolateral portion of the anterior-most extent of the region surrounding the ventricle of a neonatal rat brain and culturing the isolated cells in the absence of mitotic inhibitors.

The instant invention also provides an isolated cellular composition comprising greater than about 50% mammalian, non tumor-derived, neuronal progenitor cells which express a neuron-specific marker and which give rise to progeny which can differentiate into neuronal cells.

BRIEF DESCRIPTION OF THE DRAWINGS

FIG. 1 shows the homotopic transplantation procedure. (A) shows the SVZa, situated between the antero-lateral portion of the lateral ventricle and the overlying corpus callosum, microdissected from a sagittally sectioned neonatal (P0–P2) forebrain. (B) shows pieces of tissue containing the neuronal progenitor cells of the SVZa which were collected together, trypsinized, washed and mechanically dissociated by trituration into single cells or small clumps. (C) shows the cell suspension which was carefully washed, evaluated for viability, then labeled by the fluorescent, lipophilic dye PKH26 or BrdU to ensure the unequivocal identification of transplanted SVZa cells in the host brain. (D) shows the dissociated, PKH26 labeled SVZa cells stereotaxically placed into the SVZa of a host brain.

DETAILED DESCRIPTION OF THE INVENTION

Figure 2A:
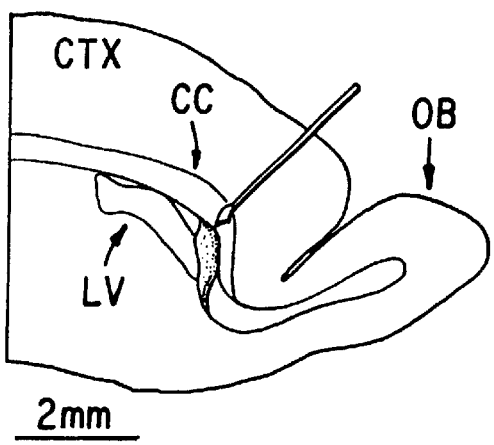
FIG. 2 shows the heterotopic transplantation procedure for transplanting P0–P2 SVZa neuronal progenitor cells into the neonatal striatum. (A) shows a representative drawing of a parasagittal section of the neonatal rat forebrain showing the location of the SVZa (black area). The SVZa was microdissected from the P0–P2 rat forebrain using a microknife (B) shows the individual tissue pieces collected in an Eppendorf tube and dissociated using fire polished Pasteur pipettes to obtain a single cell suspension of SVZa cells. (C) shows the SVZa cell suspension labeled with PKH26, a lipophilic red fluorescent dye. (To label the SVZa cells with the cell proliferation marker, BrdU, P0–P2 pups were injected intraperitoneally with BrdU. A day later the SVZa was dissected and dissociated into a cell suspension). (D) shows the labeled SVZa cell suspension stereotaxically implanted into the striatum (ST) at P0–P2. CC, corpus callosum; CTX, cerebral cortex; D, dorsal; LV, lateral ventricle; OB, olfactory bulb; P, posterior. Scale bar in (A)=2 mm and also applies to (D).
Figure 2B:
Figure 2C:
Figure 2D:
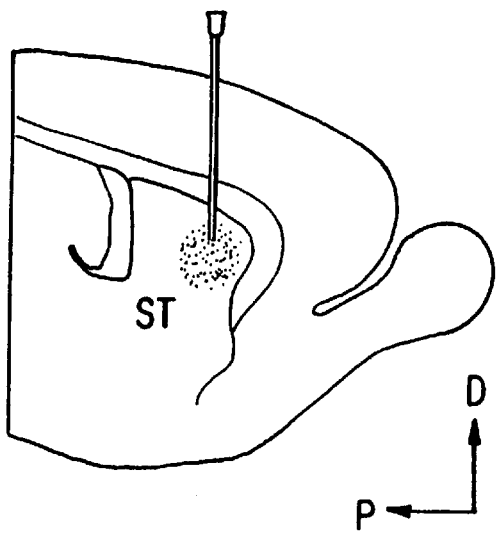

The present invention may be understood more readily by reference to the following detailed description of specific embodiments and the Examples included therein.

The present invention provides an isolated cellular composition comprising greater than about 90% mammalian, non tumor-derived, neuronal progenitor cells which express a neuron-specific marker and which can give rise to progeny which can differentiate into neuronal cells. Preferably at least about 95%, and more preferably greater than about 98%, of the composition is mammalian, non-tumor-derived, neuronal progenitor cells which express a neuron-specific marker and which can give rise to progeny which can differentiate into neuronal cells. By "isolated," as used in the claims, is meant removed from the mammalian brain. As described herein, a region of the anterior subventricular zone (SVZa) isolated from a mammalian brain is shown herein to provide a cellular composition of greater than about 90% neuronal progenitor cells which express a neuron-specific marker and which can give rise to progeny which can differentiate into neuronal cells. Compositions can also be obtained having, for example, about 50, 60, 70, 80 or 85% neuronal progenitor cells which express a neuron-specific marker and which can give rise to progeny which can differentiate into neuronal cells. Preferably, greater than about 95%, or even more preferably, greater than about 98%, of the cells in the composition are neuronal progenitor cells which express a neuron-specific marker and which can give rise to progeny which can differentiate into neuronal cells. Particularly at the time of isolation, about 98 to 100% of the cells in the composition can be neuronal progenitor cells which express a neuron-specific marker and which can give rise to progeny which can differentiate into neuronal cells. Thus, the invention provides a substantially homogeneous composition of neuronal progenitor cells.

As used herein, "neuronal cells" or "neurons" includes cells which are post-mitotic and which express one or more neuron-specific markers. Examples of such markers can include but are not limited to neurofilament, microtubule-associated protein-2, and tau, and preferably neuron-specific Class III β-tubulin and new N. As used herein "neuronal progenitor cells" are cells which can give rise to progeny which can differentiate into neuronal cells, but, unlike neuronal cells, are capable of cell division in vivo or in vitro, and which also, like post-mitotic neurons, express a neuron-specific marker.

In these compositions, preferably only about 10%, or more preferably about 5%, or even more preferably about 2%, or fewer of the cells in the composition are non-neuronal cells. Non-neuronal cells include cells which express a glia-specific marker, such as glial fibrillary acidic protein (GFAP), or which do not express any neuron-specific markers. Non-neuronal cells can include but are not limited to glial cells, subependymal cells, and fibroblasts and do not include neuronal progenitor cells.

As used herein, the "progeny" of a cell can include any subsequent generation of the cell. Thus, the progeny of a neuronal progenitor cell can include, for example, a later generation neuronal progenitor cell, a later generation cell that has undergone differentiation, or a fully differentiated, post-mitotic neuronal cell.

It must be noted that, as used in the specification and the appended claims, the singular forms "a," "an" and "the" include plural referents unless the context clearly dictates otherwise.

The present invention provides a cellular composition comprising mammalian, non-tumor derived cells which express a neuron-specific marker and which can divide. The cellular composition can be isolated from the region corresponding to the anterior portion of the subventricular zone (termed "SVZa" interchangeably herein) region of rat brain as described further herein and exemplified in the Examples below. The substantially homogeneous composition can be obtained in the absence of treatment with mitotic inhibitors. In addition, the ability of the cells to divide can be achieved in the absence of immortalization techniques. The neuronal progenitor cells can, without being first immortalized, divide for at least two generations. At least about two, preferably at least about five, and more preferably at least about ten or more generations of dividing neurons can result when the isolated cells are placed in standard culture conditions as exemplified in the Examples below.

Additionally, the cells of the substantially homogeneous composition of neuronal progenitor cells can give rise to progeny which can differentiate into neuronal cells. By use of this composition, therefore, one can obtain, in the absence of mitotic inhibitors, a composition comprising greater than 90%, and preferably greater than 95%, and more preferably greater than 98%, of any of the following cells: neuronal progenitor cells, progeny of neuronal progenitor cells and neuronal cells.

The cells comprising the herein described composition can be isolated from the SVZa of the brain of any mammal of interest. For example, cells can be obtained from mouse, rat, monkey and human. Preferred sources can be postnatal rat and mouse and prenatal monkey and human brain, though many other sources will be apparent to the practitioner. The SVZa in rat is the dorsolateral portion of the anterior-most extent of the subventricular zone surrounding the ventricles. It is anterior and dorsal to the striatum. It is whiter and more opaque than the overlying corpus callosum, presumably because of the density of cells in the region. Additionally because of the cell density, the region appears more dense and uneven. In other mammals such as human, monkey and mouse, the corresponding region can be located by both this location within the brain and by these physical characteristics.

The present invention provides a cellular composition wherein at least a portion of the cells are transfected by a selected nucleic acid. The cells can be transfected with an exogenous nucleic acid as exemplified in the Examples below. "Exogenous" can include any nucleic acid not originally found in the cell, including a modified nucleic acid originally endogenous to the cell prior to modification. By "transfected" is meant to include any means by which the nucleic acid can be transferred, such as by infection, transformation, transfection, electroporation, microinjection, calcium chloride precipitation or liposome-mediated transfer. These transfer methods are, in general, standard in the art (see, e.g., Sambrook et al., *Molecular Cloning: A Laboratory Manual,* 2nd Ed., Cold Spring Harbor Laboratory, Cold Spring Harbor, N.Y. (1989)). Preferably at least about 3%, more preferably about 10%, more preferably about 20%, more preferably about 30%, more preferably about 50%, and even more preferably about 75% of the cells, at least initially after transfection, are transfected. To increase the percentage of transfected cells, multiple transfections can be performed. For example, one can infect cells with a vector of choice, remove the media after infection, reinfect, etc. and repeat the process to achieve the desired percentage of infected cells. Some viruses, for example, can be viable for about two hours at a 37° C. incubation temperature; therefore, the infection can preferably be repeated every couple of hours to achieve higher percentages of transfected cells. Other methods of increasing transfected cell number are known and standard in the art.

Any selected nucleic acid can be transferred into the cells. For example, a nucleic acid that functionally encodes a biologically active molecule can be transfected into the cells. Preferable nucleic acids can include, for example, nucleic acids that encode a biologically active molecule that stimulates cell division or differentiation such as, for example, growth factors, e.g., nerve growth factor (NGF), brain-derived neurotrophic factor (BDNF), neurotrophin (NT)-3 and NT4/5, ciliary neurotrophic factor (CNTF), and factors that block growth inhibitors.. Additionally, preferable nucleic acids can include nucleic acids that encode a biologically active molecule that functions in the synthesis of a neurotransmitter, such as tyrosine hydroxylase (TH) and glutamic acid decarboxylase (GAD). The nucleic acid can be in any vector of choice, such as a plasmid or a viral vector, and the method of transfer into the cell can be chosen accordingly. As known in the art, nucleic acids can be modified for particular expression, such as by using a particular cell- or tissue-specific promoter, by using a promoter that can be readily induced, or by selecting a particularly strong promoter, if desired.

The present invention also provides methods for isolating the cellular compositions. Thus, methods are provided for isolating a substantially homogeneous composition in the absence of special culture conditions or treatment with mitotic inhibitors and for transfecting at least a portion of the neuronal progenitor cells or their progeny with exogenous DNA. Specifically, the present invention provides a method of obtaining an isolated cellular composition wherein greater than about 90%, and preferably greater than about 95%, and even more preferably greater than about 98%, of the cells of the composition are non-tumor-derived, neuronal progenitor cells which express a neuronal marker and which can give rise to progeny which can differentiate into neuronal cells, comprising isolating cells from the anterior portion of the subventricular zone (SVZa) of a mammalian brain and culturing the cells in the absence of mitotic inhibitors. As discussed above, sources of such cells can preferably be postnatal rat or mouse and prenatal monkey or human brain. The cells are isolated from the SVZa of the selected mammal, as described herein and exemplified in the Examples. The SVZa is located by both its location, as described and exemplified herein, and its physical characteristics, as described and exemplified herein. The cells can then be cultured in the absence of mitotic inhibitors. Thus, the cellular composition, as isolated, can be substantially devoid (i.e., comprises less than 10%, preferably less than 5%, more preferably less than 2%) of glial and other non-neuronal cells, and thus culture conditions designed to eliminate non-neuronal cells from the compositions can often be omitted. Therefore, the cultured cells are not subjected, for example, to mitotic inhibitors. However, if desired, mitotic inhibitors an be utilized. Additionally, the isolated cells can be transfected with an exogenous nucleic acid so that at least a portion of the population is transfected. Furthermore, the cells of the isolated cellular composition can be immortalized by standard methods, such as transformation, to create a cell line (see, e.g., Gage, F. H. et al., *Annu. Rev. Neurosci.* 18:159 (1995)).

The present invention also provides methods for delivering biologically active molecules produced by the neuronal progenitor cells of the composition or their progeny into a region of the brain by transplantion of the cellular composition. Specifically, the present invention provides a method of delivering a biologically active molecule produced by the neuronal progenitor cells of the composition or their progeny or mixtures thereof described above (which composition comprises an isolated cellular composition of mammalian, non-tumor-derived, neuronal progenitor cells of which greater than about 90%, preferably greater than about 95%, and preferably greater than about 98%, express a neuron-specific marker and can give rise to progeny which can differentiate into neuronal cells) to a region of a mammalian brain comprising transplanting the cellular composition into the region of the brain, thereby delivering a biologically active molecule produced in the cells to the region. The neuronal progenitor cells of the composition or their progeny or mixtures thereof can be transplanted to a host brain, either without being previously cultured or following culture. Culturing can preferably be performed according to standard conditions for neuronal cells or in defined medium with growth factors, as exemplified herein and known in the art. Cells can be cultured for any desirable length of time. For example, cells can be cultured for several days, which can expand the number of cells. For example, the neuronal progenitor cells can be allowed to divide at least once, more preferably twice, five times or ten times or more prior to transplant. Additionally, the cells transplanted prior to differentiation can divide in vivo after transplantation. Furthermore, cells for transplantation can be transfected with an exogenous nucleic acid, and the cells can undergo several rounds of transfection with an exogenous nucleic acid prior to transplantation.

Transplantation can be performed for the purpose of delivering to the host brain biologically active molecules normally produced by the transplanted cells (i.e., endogenously-encoded products) or for the purpose of delivering to the host brain biologically active molecules resulting from exogenously introduced DNA in transfected cells that are then transplanted. The term "biologically active molecules," as described also above, includes but is not limited to synthetic enzymes, neurotransmitters, putative neurotransmitters, neurotrophic factors, and factors that can block inhibitors of cell division and/or differentiation.

Transplanting, as known in the art, can be, for example, a stereotaxic injection of a cell suspension, and this injection can be into either a homotopic or heterotopic brain region. Transplantation can be performed as exemplified in the Examples herein. (Dunnett, S. B. and Björklund, A., eds., *Transplantation: Neural Transplantation—A Practical Approach*, Oxford University Press, Oxford (1992)) Cells, for example, can be suspended in a buffer solution, or alternatively whole tissue comprising the cellular composition, can be transplanted. Dissociated cell suspensions can maximize cell dispersion and vascularization of the graft. Poor vascularization is a significant factor in poor graft survival. Cells can be labeled prior to transplant, if desired. Multiple transplants can be performed, depending upon the number of transplanted cells desired to be transplanted and the area of the target region that receives the transplanted cells. Transplanted cells can preferably divide in vivo after transplantation for a limited number of generations, to create a larger region of neuronal progenitor cells and larger numbers of the cells without generating tumor formation. Additionally, transplanted cells can preferably migrate or spread out somewhat within the brain and thus create a larger region receiving these cells. Furthermore, transplanted cells can preferably eventually differentiate into mature neurons.

The present invention provides a method of treating a variety of neuronal disorders or diseases which the provision of a biologically active molecule can treat. By "treating" is meant causing an improvement in any manifestation of the specific disorder or disease. The disorders include but are not limited to disorders characterized by a reduction of catecholamines (such as Parkinson's Disease), by a reduction of GABA (such as certain forms of epilepsy and Huntington's Disease), or by neurodegenerative conditions (such as Alzheimer's Disease). To treat the specific disorder/disease, transfected or non-transfected cells of the compositions or their progeny or mixtures thereof can be transplanted into the host brain wherein the host brain demonstrates the neuronal disorder. The transplantation provides to the brain biologically active molecules produced by the transplanted cells, whether the molecules are endogenous to the transplanted neuronal progenitor cells or their progeny or whether a nucleic acid encoding the molecules were transfected into the transplanted neuronal progenitor cells or their progeny prior to transplantation. Additionally, for example, the cells can be treated prior to transplantation in a manner to cause increased production of the biologically active molecule. Alternatively the cells can be used as a source of the appropriate growth factors to treat the disease. Relatedly, the cells can be used to screen for novel growth factors which in turn could be screened for therapeutic potential.

Therefore, in one embodiment, cells can be selected for transplantation that will provide a specific biologically active molecule that will treat the specific disease of the subject. For example, for a subject having a disorder characterized by a reduction of catecholamines (such as Parkinson's Disease (PD)), the substantially homogeneous composition comprising isolated neuronal progenitor cells or their progeny, or mixtures thereof, as described above, can be transplanted, for example, for PD, into the region of the striatum. The transplanted cells need not have an exogenous nucleic acid transfected into them, as at least a portion of the cells can produce catecholamines, particularly dopamine. However, if desired, the cells can be transfected with an exogenous nucleic acid prior to transplantation. For example, recombinant nucleic acids encoding enzymes that produce higher than normal levels of the desired biologically active molecule can be utilized, if desired. Other desirable manipulation of the cells will be apparent to the practitioner, in light of the teachings herein.

Another example is treatment of a subject having a disorder characterized by a reduction of GABA, such as certain forms of epilepsy (*Merritt's Textbook of Neurology*, 9th ed. (L. P. Rowland, ed. Williams and Wilkins, Baltimore, 1995)), and Huntington's Disease (HD)) (Martin, J. B. & Gusella, J. F. *Huntington's Disease:Pathogenesis and Management*, New Eng. J. Med. 315:1267–1276 (1986)). These subjects can be treated by transplanting into the brain (e.g., into regions such as the cerebral cortex and striatum) cells of the composition or their progeny or mixture thereof as described herein. These cells need not have an exogenous nucleic acid transfected into them, since at least a portion of the cells can produce GABA. However, if desired, the cells can be transfected with an exogenous nucleic acid. For example, recombinant nucleic acids encoding enzymes that produce higher than normal levels of the product can be utilized, if desired. Other desirable manipulation of the cells will be apparent to the practitioner, in light of the teachings herein. The cells can be transplanted, for example, into regions such as the hippocampus and/or the cerebral cortex, for epilepsy, and the striatum, for Huntington's Disease.

Another example for treatment is neurodegenerative conditions, for example, Alzheimer's Disease. (R. D. Terry, R. Katzman and K. L. Bick, Alzheimer's Disease, Raven Press, NY (1994)). A cellular composition as described herein comprising cells into which has been transfected, for example, a nucleic acid encoding a biologically active molecule that stimulates cell division or differentiation (such as growth factors e.g., nerve growth factor (NGF), brain-derived neurotrophic factor (BDNF), neurotrophin (NT)-3 and NT-4/5 and ciliary NTF, or factors that block growth inhibitors), so as to decrease the amount of degeneration, can be transplanted into the brain of the subject (e.g., into regions such as basal forebrain, hippocampus, and/or cerebral cortex). Other desirable manipulation of the cells will be apparent to the practitioner, in light of the teachings herein. The cells can also be used in conjunction with various growth factors for optimal therapeutic effect. Relatedly the cells can be administered with various growth factors to screen factors for therapeutic value in animal models.

The present invention also provides a method of screening for markers of neuronal cells. Specifically, the present invention provides a method of screening for a marker of neuronal cells comprising obtaining the cellular composition described herein (which composition comprises greater than about 90% or 95% neuronal progenitor cells which express a neuron-specific marker and which can give rise to progeny which can differentiate into neuronal cells), obtaining non-neuronal cells or information concerning the markers of those cells, and detecting the presence of a marker in the cellular composition that is not present in non-neuronal cells, the marker present in the cellular composition that is not present in the non-neuronal cells being a marker of neuronal cells. Thus, markers of the cellular composition can be compared to markers of non-neuronal cells to identify markers present in neurons, exclusively or in greater proportions. The neuron-specific markers can be useful in diagnostic and therapeutic techniques for neuronal diseases.

Additionally, the present invention provides a method of detecting a neuronally expressed gene comprising obtaining a cDNA library from the herein described cellular composition (which composition comprises greater than about 90%, preferably greater than about 95%, and more preferably greater than about 98%, mammalian, non-tumor-derived neuronal progenitor cells which express a neuron-specific marker and which can give rise to progeny which can differentiate into neuronal cells), obtaining a cDNA library from a non-neuronal cell, determining the presence at higher levels of a cDNA in the library from the cellular composition than in the non-neuronal cell, the presence at higher levels of a cDNA in the library from the cellular composition indicating a neuronally expressed gene. Thus, cDNA libraries derived from the neuronal composition can be compared to a cDNA library from non-neuronal cells to identify genes expressed exclusively or in greater proportions in neuronal cells. Methods of performing such comparative screenings are known in the art, and thus can be readily performed by the artisan given the teachings herein. The neuron-specific markers could be useful in diagnostic and therapeutic techniques for neuronal diseases.

Utility of the Invention

Because mammalian neurons are generally incapable of dividing when mature, sources of dividing neuronal cells have been sought. The present invention provides a source of such dividing cells. These cells additionally demonstrate characteristics of neuronal cells. Therefore, the cellular composition provides a useful composition for, for example, transplanting healthy cells having a neuronal phenotype into subjects whose neurons are degenerating or are not producing normal cellular molecules. The transplanted cells can then provide the deficient molecule(s) to the brain. For example, the present composition can be particularly useful for treating Parkinson's disease (PD), which is characterized by a reduction in catecholamines, by transplanting the inventive cellular composition into the brains of subjects having PD. The transplanted cells can then provide catecholamines to the brain. Another example in which the present composition can be useful is in treating Huntington's Disease or in forms of epilepsy characterized by a reduction in GABA, because these cells can provide GABA to a brain into which they are transplanted. Furthermore, the composition can be useful in providing the desired product of any nucleic acid into the central nervous system. Any desired nucleic acid can be transfected into the neuronal progenitor cells of the composition and transplanted into the central nervous system. An example of a disease that can be treated by such a method is Alzheimer's disease (AD). Cells having a nucleic acid encoding, for example, a growth factor or a neurotrophic factor, can be injected into the brains of AD patients to decrease or prevent degeneration in the brain.

The present compositions additionally can be used to screen for markers of neuronal cells and can be used to further characterize and identify new neuronal cells. The markers can be used for example to detect or treat disease conditions or to identify the anterior portion of the subventricular zone in mammals. Such cells can also be utilized to screen for compounds that affect neuronal cells, either positively or adversely. In this manner, compounds (e.g. novel growth factors) for treating neuronal disorders can be screened, and compounds harmful to neurons can be determined. Many other uses in diagnosis and treatment of neuronal diseases will be apparent to the artisan. The invention can be utilized in therapeutic treatment of any neuronal disease or disorder in which the provision of a healthy neuron and/or a neuron expressing a desirable gene can alleviate some effects of the disease or disorder. Thus, it can have widespread uses, as will be apparent to the skilled artisan given the teachings herein.

The cells can also be used to produce neuronal growth factors for therapy or use as research tools in cell differentiation. The cells themselves can also be used as a research tool to study cell growth and differentiation.

The present invention is more particularly described in the following Examples which are intended as illustrative only since numerous modifications and variations therein will be apparent to those skilled in the art.

EXAMPLES

The present invention is more particularly described in the following Examples which are intended as illustrative only since numerous modifications and variations therein will be apparent to those skilled in the art.

Example 1
Microdissection and Dissociation of SVZa Cells

A method was devised to microdissect the SVZa from parasagittal sections of the newborn rat brain. To harvest SVZa cells, P0–P1 Sprague-Dawley pups were anesthetized on ice, decapitated and their heads placed in cold sterile Ham's F-10 medium (Sigma). After removing the skull, the brain was placed in fresh medium and bisected at the midline. Under the dissecting microscope approximately 2 mm thick parasagittal sections were taken from the midline of the hemispheres and the SVZa microdissected as illustrated in FIG. 1. The SVZa is the dorsolateral portion of the anterior-most extent of the region surrounding the ventricles. It is anterior and dorsal to the striatum. The SVZa can be distinguished from the surrounding structures by its position relative to the ventricle as well as by its coloration and texture. SVZa is white and more opaque than the overlying corpus callosum because it is so cell dense relative to the corpus callosum. The SVZa also appears more dense and uneven because of the cell density. In the neonatal rat, the SVZa can be found at approximately 2.0 mm anterior to bregma, 1.0 mm lateral to the midline and 2.0 mm deep to the pial surface.

Pieces of SVZa tissue from several (7–12) pups were pooled in a sterile test tube containing approximately 5 ml of Hank's balanced salt solution (HBSS). The pieces were incubated for 20 min at 37° C. in a 0.1% trypsin and 0.01% DNase in HBSS and washed with medium containing 0.04% DNase in HBSS. The last wash volume was brought up to 5 $\mu$l per dissected tissue piece, resulting in $10^5$–$10^6$ cells/ml. To achieve relatively even dissociation into single cells and small clumps, the tissue was thoroughly triturated.

Before transplantation or culture, cell viability was determined using the fluorescent FDA/PI (fluorescein diacetate/propidium iodide) method providing positive identification of living (green) and dead (red) cells. A viability of 80–95% has been routinely obtained from the freshly prepared cell suspensions.

Example 2
Cell labelling in vitro

In order to visualize cells transplanted into a host brain, the cells can be labelled with the lipophilic membrane bound dye, PKH26, which fluoresces red with a 551 nm excitation and 567 nm emission, can be used to label the dissociated SVZa cells immediately prior to transplantation. For the SVZa cells, the freshly dissociated cell suspension was labelled with PKH26 (4 M dye in diluent C, Sigma) for 3–5 min. Virtually all cells become intensely labeled.

In some experiments, BrdU (5 mg BrdU/ml of 0.007 N NaOH in 0.9% NaCl), a cell proliferation marker, has been used to label dissociated SVZa cells prior to transplantation. Using this labelling method, dividing cells can be visualized after transplantation according to the procedure described by Menezes and Luskin J. Neurosci. 14:5399 (1994). Specifically, bromo-deoxyuridine (BrdU) was added to the culture media, and then 1 to 24 hours later the cultures were fixed as described above and stained with antibodies to BrdU to reveal the presence of labeled cells. After fixation, the cultures were washed with 0.01 M PBS and treated with 2N HCI at 60° C. to fragment the DNA followed by acid neutralization in 0.01 M borate buffer, pH 8.3. After a thorough wash with PBS and application of blocking serum (10% normal goat serum with 0.01% Triton X-100 in 0.01 M PBS), the cultures were incubated overnight with a monoclonal antibody to BrdU (a-BrdU, Accurate, N.Y.), at 4° C. using a 1:500 dilution. Afterwards the cultures were rinsed with 0.1 M PBS and incubated with a rhodamine conjugated goat anti-rat secondary antibody (Jackson ImmunoResearch, PA) at a 1:200 dilution for I hour at room temperature, washed in 0.1 M PBS and coverslipped using Vectashield (Vector, Calif.). BrdU-positive cells display a red fluorescent nucleus.

Example 3
Cell culture

The isolated SVZa cells in culture are essentially all neuronal, i.e., they are immunoreactive when stained with neuron-specific markers. To ascertain the phenotype of the harvested and dissociated SVZa cells, they were plated on uncoated glass microscope slides or poly-D-lysine or poly-ornithine coated glass slides and cultured in either full strength Ham's F10 medium (Sigma) or Dulbecco's minimal essential medium DMEM (Sigma) supplemented with 10% fetal calf serum or 1:1 ratio of Ham's F10 medium:DMEM, at 37° C. in 7% $CO_2$. Specifically, following dissociation, the cells were centrifuged at 700 rpm for 7 min, the pellet redispersed in new medium and the number of cells estimated using a hemacytometer. Approximately $3.32 \times 10^3$ cells were added to each well of the glass chamber slides (LabTek 16 well). Each well was coated with 10 μg/ml of poly-D-lysine (P-7280, Sigma) for 1 h at 37° C. in the incubator, rinsed 3 times with distilled water and air dried in the culture hood. Alternatively, the cells were plated on 10 μg/ml of mouse laminin (23017-015, Gibco), on 500 μg/ml poly-L-ornithine (P-3655, Sigma) or on a combination of both.

One to eight days later the SVZa cultures were fixed for 20 min in 4% paraformaldehyde and 0.12 M sucrose in 0.1 M PBS, rinsed in cold PBS, permeabilized with 100% ethanol, rehydrated in an ethanol series and rinsed in PBS. After incubation in 50 mM glycine and three rinses in cold PBS, blocking serum (0.5% normal goat serum and 0.01% Triton X-100 in 0.1 M PBS) was applied for 1 hour. Cells were incubated overnight with a 1:500 dilution of the mouse monoclonal antibody TuJ1, a neuron-specific antibody recognizing class III β-tubulin (Lee et al., *Proc. Natl. Acad. Sci.* 87:7195 (1990)); supplied by Dr. A. Frankfurter, University of Virginia, Charlottesville, Va.) and a rabbit polyclonal antibody (GFAP; Dako) to glial fibrillary acidic protein (Bignami et al., *Brain Res.* 43:429 (1972)) at a dilution of 1:500. Cells were then rinsed in 0.1 M PBS and incubated for an hour in a mixture of secondary antibodies including fluorescein goat anti-mouse (Jackson, 1:100) and rhodamine goal anti-rabbit (Jackson, 1:200), washed in 0.1 M PBS, pH 7.4, coverslipped using Vectashield (Vector, CA) and examined by epifluorescence microscopy.

After one day in vitro (1 DIV) all or nearly all of the cultured SVZa cells stained with TuJ1. When viewed by bright-field and phase microscopy within the first few hours after plating, the vast majority of cells adhered to the surface of the glass slide and some even extended one or two processes from their cell bodies. This indicates that some of the plated cells began to differentiate almost immediately after plating.

To ascertain definitively the identity of the microdissected cells prior to transplantation, cells were plated and stained for cell-type specific markers to characterize them. Characterizing the identity of the cells was done to determine the purity of the dissected cells and whether the microdissected cells contained progenitors for glia. As described above, the viability of the dissociated cells prior to plating was quite high; between 80–95 per cent. When viewed by bright-field and phase microscopy within the first few hours after plating, the vast majority of cells adhered to the surface of the glass and some even extended one or two processes from their cell bodies. This indicates that some of the cultured cells began to differentiate almost immediately after plating. TuJ1, an antibody that recognizes neuron-specific class III β-tubulin (Lee et al., *Proc. Natl. Acad Sci.* 87:7195 (1990)), was used to identify cells with a neuronal phenotype and an antibody to GFAP to distinguish astrocytes, a cell type commonly derived from other regions of the neonatal subventricular zone (Privat, *Int. Rev. Cytol.* 40:281 (1975); Levison and Goldman, *Neuron* 10:201 (1993); Luskin and McDermott, *Glia* 11:211 (1994)).

After 24 hours in culture, the majority of the cultured cells either occurred in small clusters containing 2–4 cells or as individual cells with a bipolar or occasionally multipolar morphology. Interestingly, the overwhelming majority of clustered and individual cells exhibited distinct TuJ1 immunoreactivity, apparent in the somatic cytoplasm and cell processes. At this stage, GFAP-positive cells in the cultures were rarely seen. The result showed that the plated cells possess a pronounced neuronal identity. This result also indicated that only the SVZa was included in the dissection. If this were not the case, GFAP-positive cells would be expected.

Cells were also stained at intermediate times up to 8 days in culture to discern what proportion of the cells exhibit exclusively a neuronal phenotype. At 8 days, the cultured cells occurred in small clumps or were loosely arranged and that the cells now extended numerous intermingling processes. Again, nearly all of the cells expressed prominent TuJ1 immunoreactivity. As in the short-term cultures, glia, as signified by GFAP-immunoreactivity, represented less than 5% of all cultured cells. These findings demonstrated that the region of the SVZa which contains a seemingly pure population of neuronal progenitor cells can be isolated.

Since many types of neurons exhibit substrate-dependent process outgrowth, the ability of SVZa-derived cells to extend processes was tested on different substrates. SVZa cells were found to extend processes on poly-D-lysine at 10 μg/ml and on poly-L-ornithine (or on poly-D-L-ornithine) and exhibited monopolar, bipolar and multipolar morphologies. However, in contrast to cerebellar granule neurons, on 10 μg/ml laminin, SVZa cells did not sprout.

Another unexpected property of the cultured SVZa cells is that they proliferate in culture. This was surprising because most cells expressing neuron-specific cell markers are post-mitotic cells (Moody et al., *J. Comp. Neurol.* 279:567 (1989); Menezes and Luskin, *J. Neurosci.* 14:5399 (1994). Furthermore, it is often difficult to establish conditions under which cells giving rise to neurons can divide in culture (Reynolds and Weiss, *Science* 255:1707 (1992). Not only did the cultured SVZa cells divide immediately after plating, but they also divided several days after they have been cultured.

To demonstrate that cultured SVZa cells undergo division, the cell proliferation marker bromo-deoxyuridine (BrdU) was added to the culture media, and then 1 to 24 hours later the cultures were fixed as described above and stained with antibodies to BrdU to reveal the presence of labeled cells. After fixation, the cultures were washed with 0.01 M PBS and treated with 2N HCI at 60° C. to fragment the DNA followed by acid neutralization in 0.01 M borate buffer, pH 8.3. After a thorough wash with PBS and application of blocking serum (10% normal goat serum with 0.01% Triton X-100 in 0.01 M PBS), the cultures were incubated overnight with a monoclonal antibody to BrdU (α-BrdU, Accurate, NY), at 4° C. using a 1:500 dilution. Afterwards the cultures were rinsed with 0.1 M PBS and incubated with a rhodamine conjugated goat anti-rat secondary antibody (Jackson ImmunoResearch, PA) at a 1:200 dilution for 1 hour at room temperature, washed in 0.1 M PBS and coverslipped using Vectashield (Vector, CA). BrdU-positive cells display a red fluorescent nucleus.

Example 4

Homotopic transplantation of SVZa cells

To investigate the migratory behavior of homotopically transplanted SVZa-derived cells, dissociated donor rat SVZa cells were implanted in the neonatal SVZa of a rat host. The purpose of the experiment was to determine if transplanted cells are able to read the same guidance cues and attain the same laminar distribution in the host brain as unmanipulated SVZa-derived cells. Dissociated SVZa cells rather than explants of tissue were transplanted to facilitate the integration of the transplanted cells in the host brain.

In order to analyze the migratory behavior of homotopically transplanted SVZa cells, the distribution of transplanted cells at 3 postimplantation time periods was examined: short survivals (after 1 week or less), intermediate survivals (after 2 to 3 weeks) and long survivals (4 weeks or longer). The experiment was performed to find out if the distribution of the transplanted cells matched that of the unmanipulated cells at the various time points chosen for study. From our in vivo studies in which PKH26 was directly injected into the SVZa to label its cells, the time periods chosen for analysis correspond to when SVZa-derived cells would occur predominantly in the pathway, subependymal zone of the olfactory bulb and overlying granule cell layer, and when they are in their final positions in the granule cell and glomerular layers.

Short-term Survival

To compare the overall distribution and dynamics of cell movement by unmanipulated SVZa-derived cells to that of transplanted SVZa cells, dissociated PKH26-labeled SVZa cells were injected into the host SVZa. To visualize PKH26 labelled cells in vivo, animals were perfused with 4% paraformaldehyde, their brains removed, and sectioned on a Vibratome. Serial 100 $\mu$m sections were mounted and examined by fluorescence microscopy for PKH26-labeled cells. The subsequent position and morphology of the cells were examined within one week after transplantation.

Examination of host brains 1 day after transplantation revealed that the injection site was usually centered in the SVZa and that it usually contained a high density of PKH26-labeled cells. At the injection site the red fluorescing PKH26-labeled cells were small and round. These cells usually occurred as individual cells or in small clumps, resembling freshly dissociated cells.

The path of migration demonstrated by transplanted SVZa cells matches precisely the path followed by unmanipulated SVZa-derived cells. It constitutes a long pathway connecting the SVZa to the center of the olfactory bulb measuring several millimeters. At progressively longer times after transplantation the distribution of labeled cells extended further from the site of implantation.

By two days after transplantation, a continuous stream of cells was observed coming from the rostral wall of the anterior horn of the lateral ventricle (SVZa) to the vertical limb of the pathway. By four days after transplantation the labeled cells were in the horizontal arm of the pathway, and some cells reached the central part of the olfactory bulb. At the end of the first week after transplantation, migrating cells were found evenly distributed throughout the subependymal layer extending from the SVZa to the middle of the olfactory bulb. Moreover, as found for the unmanipulated SVZa-derived cells, the transplanted cells were strictly confined to the well-defined pathway characterized by a region of high cell density. This demonstrates that the transplanted PKH26labeled SVZa cells faithfully acknowledge the boundaries of the migratory pathway and do not deviate from it.

Fluorescence microscopy revealed that the majority of transplanted PKH26-labeled cells have a round soma, and that some have a relatively short and thick process extending toward the olfactory bulb. Within the subependymal zone of the olfactory bulb, many transplanted cells have an oval or spindle-shaped soma with a clear, unlabeled nucleus. In contrast to the unmanipulated SVZa-derived cells, at this stage only a low number of dye-labeled cells revealed processes. One possibility to account for the differential labeling of SVZa-derived cells is that perhaps the PKH26 does not label the transplanted cells in their entirety Alternatively, perhaps some transplanted cells lack fully developed processes In this case the transplanted cells may be able to reach the bulb by becoming incorporated into the stream of unmanipulated SVZa-derived cells which are also traveling to the olfactory bulb.

Intermediate Survival

Distribution of transplanted cells in the migratory pathway and granule cell layer of the olfactory bulb. By two weeks after transplantation some of the transplanted cells had advanced into the granule cell layer of the olfactory bulb. It appeared as though the labeled cells had moved from the subependymal layer of the bulb into the overlying granule cell layer. Concomitantly, there was a striking reduction in the proportion of transplanted cells in the more caudal parts (vertical limbs) of the migratory pathway. By three weeks after transplantation a greater proportion the donor cells had entered the granule cell layer, leaving fewer in the subependymal zone and pathway distal to the olfactory bulb.

When the transplanted cells turned radially from the subependymal zone towards the granule cell layer, some of them began to differentiate into granule cells, revealing two PKH26-labeled processes. The transplanted cells within the granule cell layer, which presumably are undergoing differentiation, had the characteristic bipolar morphology of maturing, unmanipulated granule cells. The range of mature and immature morphologies seen among the PKH2labeled cells 2–3 weeks after homotopic transplantation indicates that the cells are at various stages of differentiation. In fact, some of the PKH26labeled cells in the granule cell layer appeared to be still en route to the glomerular layer, judging by their spindle-shaped cell soma which is characteristic of migrating neurons.

In some experiments BrdU incorporation was used to label SVZa cells before transplantation. BrdU-labeled cells were visualized according to the procedure described by Menezes and Luskin *J. Neurosci* 14:5399 (1994). In brief, brains were perfused with 4% paraformaldehyde and then cryoprotected overnight in 20% sucrose in 0.1 M phosphate buffered saline (PBS). The brains were embedded in Tissue Tek O.C.T. Compound, sagittally sectioned on a cryostat at 18–20 $\mu$m and mounted on slides before processing for the presence of BrdU. The sections were washed with 0.01 M PBS and treated with 2N HCl at 60° C. to fragment the DNA followed by acid neutralization in 0.01 M borate buffer, pH 8.3. After a thorough wash with PBS and application of blocking serum (10% normal goat serum with 0.01% Triton X-100 in 0.01 M PBS), the sections were incubated overnight with a monoclonal antibody to BrdU ($\alpha$-BrdU, Accurate, NY), at 4° C. using a 1:500 dilution. Afterwards the sections were rinsed with 0.1 M PBS and incubated with a rhodamine conjugated goat anti-rat secondary antibody (Jackson ImmunoResearch, PA) at a 1:200 dilution for 1 hour at room temperature, washed in 0.1 M PBS and coverslipped using Vectashield (Vector, CA). BrdU-positive cells display a red fluorescent nucleus. The distribution of trans-planted BrdU-labeled cells matched the distribution of PKH26-labeled cells when examined after the same survival period. Two weeks after transplantation, fluorescence microscopy revealed the presence of intensely labeled BrdU-positive cells predominantly in the portion of the migratory pathway close to the olfactory bulb (horizontal limb) and in the subependymal zone of the bulb, although a few had advanced into the overlying granule cell layer. Thus, even though the BrdU labeling does not reveal the precise morphology of the transplanted cells, it clearly reveals their position.

Long Survival

Both PKH26 and BrdU labeling procedures were used to unequivocally identify the transplanted SVZa-derived cells.

In particular, there were concerns that over time the PKH26 dye intensity may diminish. Therefore, most conclusions were based on the analysis of BrdU-labeled cells.

Previous studies showed that four weeks after an injection of retrovirus into the SVZa that the SVZa-derived cells have achieved their final laminar distribution (Luskin, *Neuron* 11:173 (1993)). In these experiments, a similar laminar distribution of trans-planted cells was found. When compared with the intermediate survival, significantly higher numbers of transplanted cells were distributed throughout the granule cell layer. Another group of cells, most likely periglomerular cells, were found encircling the glomeruli. A few transplanted cells still occupied the rostral half of the subependymal layer of the olfactory bulb 4 weeks after transplantation. Thus, the sequential changes in the migratory pattern of unmanipulated SVZa cells seems to be matched by the homotopically transplanted cells. This suggests that they are able to discern the same set of guidance cues.

Quantitative analyses showed that the ratio between labeled cells in the glomerular layer and granule cell layer after transplantation was identical to what occurs in the unmanipulated brain (Luskin, *Neuron* 11:173, (1993)). Seventy-five percent of the transplanted cells ended up in the granule cell layer or adjacent to it and the other twenty-five percent were found in the glomerular layer of the olfactory bulb. Collectively, these findings suggest that transplanted SVZa-derived cells are not only able to adopt the same migratory route as their counterparts originating from the host SVZa but that they are also able to acquire the same laminar distribution between the granule cell and glomerular layers in the olfactory bulb.

Example 5
Heterotopic transplantation of SVZa cells into neonatal cerebellum ventricular zone of embryonic telencephalon, or areas adjacent to the anterior portion of the subventricular zone To make injections into the external granular layer of the neonatal cerebellum, a small incision through the skull overlying the midbrain and the hindbrain can be made and labeled SVZa cells can be injected using a Hamilton syringe into a position just beneath the meninges (Gao and Hatten, *Science* 260:367 (1993)).

To make injections into the ventricular zone of the embryonic telencephalon the procedure described by Dunnett and Bjorklund in *Transplantation: Neural Transplantation—A Practical Approach*, Oxford Univ. Press, Oxford (1992), can be followed. In brief, under deep anesthesia the abdominal wall of a pregnant dam can be incised. The uterine horns can be exposed and each fetus transilluminated with the fiberoptic tube. A pipette containing labeled SVZa cells can be inserted through the uterine wall, amniotic sac, and the fetal skull into the ventricular zone overlying the cerebral cortex.

To investigate the behavior and distribution of SVZa cells transplanted into areas adjacent to the anterior portion of the subventricular zone, SVZa cells were transplanted into position lying either posterior or lateral to the SVZa of the host. Retrovirus injections had shown that only when the injections were within the SVZa did the labeled cells end up in the olfactory bulb and become neurons (Luskin, *Neuron* 11:173 (1993), Luskin and McDermott, *Glia* 11:211 (1994)). Of the four animals used in this experiment, no labeled cells were found in the migratory pathway or in the olfactory bulb following the nonSVZa injections, confirming that SVZa provides certain positional information to guide SVZa-derived cells to the olfactory bulb.

The phenotypic identity of unmanipulated SVZa-derived cells in the mature (>6 weeks) olfactory bulb has been analyzed. The phenotype of SVZa-derived cells can be classified according to their morphology (Pinching and Powell, *J. Cell Sci.* 9:305, 347, 379 (1971)) and the neurotransmitter candidates they contain (Bartolomei and Greer, *Neurosci. Abst.* 19:125 (1993). Halasz et al. *Brain Res.* 167:221 (1979) has shown that essentially all granule cells contain GABA, as do many periglomerular cells. Periglomerular cells are also known to express tyrosine hydroxylase, the rate limiting step in the synthesis of dopamine (McLean and Shipley, *J. Neurosci.* 8:3658 (1988). Moreover, Gall et al. *J. Comp. Neurol.* 266:307 (1987), and Kosaka et al. *Brain Res.* 343:166 (1985) have independently shown the colocalization of GABA and TH in subsets of periglomerular cells. Furthermore, since Celio *Neurosci.* 35:375 (1990), Halasz et al. Neurosci. *Letters* 61:103 (1985) and Kosaka et al. *Brain Res.* 411:373 (1987) reported that virtually all periglomerular cells are immunoreactive for calbindin (28K-vitamin-D-dependent calcium binding protein), calbindin immunoreactivity can be determined in unmanipulated and transplanted BrdU-labeled SVZa cells situated in the glomerular layer express calbindin. Furthermore, the phenotype acquired by heterotopically transplanted SVZa-derived cells in the cerebellum and cerebral cortex, and that acquired by ventricular zone and EGL cells in the olfactory bulb can be examined.

Example 6
Double-Labeling

Following transplantation of BrdU-labeled SVZa cells into the SVZa, as described above, procedures have been devised to reveal the presence of BrdU and transmitter candidates or their synthetic enzymes using double label precedures on 20 μm cryostat sections. Following perfusion with 4% paraformaldehyde in 0.1 M phosphate buffer (pH 7.4) brains were removed, equilibrated in 20–30 % sucrose in 0.1 M phosphate buffer overnight and then cut sagittally or coronally at a thickness of 20 μm on a cryostat. Sections were washed in 0.1 M PBS, treated with 2N HCI at 45–50° C. for 15 minutes and subsequently rinsed with 0.1 M borate buffer, pH 8.3 for 15 minutes. Sections were then incubated in 10% normal goat serum in PBS for 30 minutes and then overnight in a mixture of primary antibodies including anti-BrdU (1:500; Accurate, NY) and an antibody to either GABA (1:500; Sigma), TH (1:1000, Eugene Tech, NJ) or calbindin (Sigma, 1:1000 dilution). The next day the sections were rinsed in 0.1 M PBS and incubated for 2 hours in an appropriate mixture of secondary antibodies that contain goat anti-rat IgG conjugated to rhodamine to visualize BrdU immunoreactive cells and FITC conjugated secondaries to identify one of the neurotransmitter candidates. Lastly the sections were rinsed in 0.1 M PBS and coverslipped.

Sections were examined with fluorescence microscopy to identify labeled SVZa cells, and their neurotransmitter phenotype and laminar position determined. The SVZa-labeled cells were evident by their red fluorescence and the transmitter labeling, when present in the same cells by green fluorescence of both unmanipulated and transplanted cells. The percentage of SVZa-derived GABAergic, TH-immunoreactive and calbindin-positive cells were determined for unmanipulated cells in each layer of the olfactory bulb.

Previous studies have shown that the SVZa-derived cells are neurons based on their laminar distribution and morphological features. To further characterize the SVZa-derived neurons in the olfactory bulb, cell-type specific markers for transmitter phenotype were used. At P20, when most of the SVZa-derived cells have reached their final destination following an SVZa injection of BrdU at P2, BrdU-labeled cells were localized using immunohistochemistry and their neurotransmitter phenotype was assessed using antibodies against gamma-aminobutyric acid (GABA) and the dopamine synthesizing enzyme tyrosine hydroxylase (TH). Using simultaneous indirect immunofluorescence to detect the presence of single- and double-labeled cells, 10% of the SVZa-derived cells were found to be both BrdU- and TH-positive in the glomerular layer and that approximately 67% and 46% of the SVZa-derived cells in the granule cell layer and glomerular layer were GABAergic (GABA- and BrdU-positive), respectively. When analyzed at P20, 28% and 12 % of the periglomerular cells, that arose from a P2 injection of BrdU were TH- and GABA-positive respectively, were found. Similarly, at P20, 11% of the GABAergic neurons in the granule cell layer were generated on P2. These results indicate that the neonatal SVZa is a source of dopaminergic cells destined for the glomerular layer and also a source of GABAergic cells for the granule cell and glomerular layers.

The transmitter phenotype of unmanipulated SVZa-derived cells in the olfactory bulb can now be compared with the transmitter phenotype expressed by homotopically and heterotopically transplanted cells that reach the olfactory bulb after implantation in the SVZa. This can allow determination of whether transplanted cells acquire the same transmitter identity as unmanipulated SVZa-derived cells, or if transmitter candidates expressed by the heterotopically transplanted cells are more representative of the transmitters they ordinarily express. If the heterotopically transplanted cells reach the periglomerular layer and express TH, then conclusions can be drawn that their identity has been respecified; dopamine is ordinarily expressed only by cells of the substantia nigra and olfactory bulb. The phenotype of unmanipulated cells can be compared to the homotopically and/or heterotopically transplanted cells, i.e., those implanted in the striatum.

Example 7
Heterotopic transplantation of cortical and cerebellar cells into neonatal SVZa In additional experiments, it was investigated whether newly-generated neurons, which usually migrate along radial glia, could navigate the highly restricted path adhered to by SVZa derived cells that appears not to be guided by radial glia. Cerebellar external granule layer (EGL) cells (postnatal) and ventricular zone (VZ) cells (prenatal) were harvested for transplantation. In brief, EGL cells were removed by suction on the surface of the cerebellum or by microdissection and then trypsin and DNase were used to dissociate the cells as described above. To harvest progenitor cells of the E16 VZ, a modified procedure used by McConnell, *Brain Res. Rev.* 13:1 (1988), was employed. Dissociated cells from the VZ of the embryonic day 15 to 17 rat telencephalon or from the EGL of the postnatal day 5 (P5) or P6 cerebellum, were labeled with either the cell proliferation marker BrdU or the fluorescent lipophilic dye PHK26 and stereotaxically implanted into the SVZa of P0–P2 rats. Results showed that heterotopically engrafted VZ cells remained at the site of infection. In contrast, heterotopically transplanted EGL 5 cells traversed the migratory pathway, although most did not migrate away from the middle of the olfactory bulb (OB).

Example 8
Heterotopic transplantation of SVZa cells into the striatum

To maximize the number of labeled SVZa cells obtained for transplantation, P0–P1 donor pups were given 2–3 intraperitoneal injections (6 hours apart) of a BrdU stock solution (5 mg BrdU/ml of 0.007 N NaOH in 0.9% saline; 0.3 ml/pup/injection). The last injection was given one hour before dissection of the donor tissue.

The SVZa cells were dissected and dissociated as described above and the viability of the cell suspension determined as described above. A viability of about 80–95% was obtained, and the cell concentration ranged from $2.9 \times 10^4$ to $5.4 \times 10^6$ cells/ml. The dissociated cells were labeled with PKH26 by incubating the freshly prepared cell suspension in a 4.0 $\mu$M solution of PKH26 dye and diluent C for 3–5 minutes according to the protocol provided by Sigma.

The dissociated and labeled SVZa cells were transplanted into the striatum of P0–P2 pups that were anesthetized by hypothermia. To reduce movement and maximize the consistency of injection coordinates, the head of the pup was placed on a Sylgard contoured mold. (To determine the coordinates for targeting the P0–P2 striatum, PKH26 was directly injected into the brains of four P0–P1 pups. The range of coordinates were chosen by comparing the results obtained from PKH26 injections as well as from a few initial transplantation experiments using implantation of labeled SVZa cells.) The injections were made between 0.8–2.0 mm anterior to bregma (A–P) and 1.2–2.3 mm lateral to the sagittal sinus (M-L) and 2.3–3.5 mm deep to the pial surface (depth). We demonstrated that injections within the following range of coordinates A-P, 1.0–1.5 mm; M-L, 1.8–2.3 mm and depth, 2.5–3.5 mm, were most likely to target the striatum (Table 1) and were in agreement with those used by Abrous et al. (1). An incision was made through the skin overlying the sagittal suture to expose the skull. A small hole was made through the skull centered around 1.8–2.3 mm lateral to the sagittal suture and 1.0–1.5 mm anterior to the bregma. A 10 $\mu$l Hamilton syringe, containing the SVZa cells, attached to a micromanipulator, was lowered approximately 2.5–3.5 mm from the pial surface and 2–4 $\mu$l of the labeled cell suspension was injected into the striatum. Following transplantation, the overlying skin was repositioned and sealed with surgical glue and the pup was placed under a heat lamp for recovery before transferring it back to its home cage. Following transplantation the pups were allowed to survive for various time periods before they were perfused. At the time of perfusion the pups were anesthetized with ether and perfused transcardially with 4% paraformaldehyde in 0.1 M phosphate buffer (pH 7.4). The brains were removed, blocked in the sagittal plane, and post-fixed in the same fixative for at least 1 h before washing with 0.1 M PBS. The BrdU and PKH26-labeled cells were detected as described above.

TABLE 1

Coordinates for implantation of SVZa cells and their subsequent distribution

| Rat Number | Age at Implantation | Survival (days) | Injection site (mm) A-P | M-L | Depth | Labeled cells: in striatum/ along striatal boundary | PKH26 or BrdU |
|---|---|---|---|---|---|---|---|
| 1 | P1 | 3 | 0.9 | 1.8 | 3.1 | +/− | BrdU |
| 2* | P1 | 5 | 0.8 | 1.7 | 2.4 | −/− | PKH26 |
| 3 | P1 | 13 | 2.0 | 1.7 | 2.3 | −/+ | PKH26 |
| 4 | P0 | 13 | 1.5 | 2.0 | 2.9 | +/− | PKH26 |
| 5 | P2 | 13 | 1.0 | 2.0 | 3.3 | +/+ | BrdU |
| 6* | P2 | 13 | 1.0 | 2.0 | 3.2 | −/− | BrdU |
| 7* | P2 | 13 | 1.0 | 2.0 | 3.2 | −/− | BrdU |
| 8 | P1 | 18 | 1.2 | 2.0 | 3.3 | +/+ | BrdU |
| 9* | P1 | 19 | 1.0 | 1.7 | 2.5 | −/− | PKH26 |

TABLE 1-continued

Coordinates for implantation of SVZa cells and their subsequent distribution

| Rat Number | Age at Implantation | Survival (days) | Injection site (mm) A-P | M-L | Depth | Labeled cells: in striatum/ along striatal boundary | PKH26 or BrdU |
|---|---|---|---|---|---|---|---|
| 10 | P0 | 20 | 1.2 | 2.0 | 2.5 | −/+ | PKH26 |
| 11* | P1 | 20 | 2.0 | 1.5 | 3.1 | −/− | PKH26 |
| 12* | P1 | 21 | 1.5 | 1.2 | 3.2 | −/− | PKH26 |
| 13 | P0 | 26 | 1.0 | 2.0 | 3.0 | +/+ | PKH26 |
| 14 | P1 | 26 | 1.0 | 2.0 | 3.0 | +/+ | PKH26 |
| 15 | P1 | 26 | 1.0 | 2.0 | 3.2 | +/− | PKH26 |
| 16 | P1 | 26 | 1.0 | 2.0 | 2.9 | +/− | BrdU |
| 17 | P1 | 26 | 0.8 | 1.2 | 3.3 | +/− | BrdU |
| 18 | P1 | 28 | 1.2 | 1.5 | 3.3 | −/+ | BrdU |
| 19 | P1 | 41 | 1.2 | 2.0 | 3.4 | +/+ | BrdU |

*Coordinates for implantation of labeled SVZa cells and their subsequent distribution. This table lists the coordinates used to determine the position of the striatum in the neonatal brain and the ensuing distribution of the transplanted SVZa cells at the time of perfusion (survival days). Postnatal day 0–2 pups were injected with PKH26- or BrdU- labeled P0–P2 SVZa cells. The reference points for the injection site coordinates wereas follows: 1.0–1.5 mm anterior to bregma (A-P); 1.8–2.3 mm lateral to the sagittal suture (M-L); and 2.5–3.5 mm deep to the pial surface (depth). The presence or absence of labeled cells in the striatum or along the striatal boundary was scored as (+) or (−) respectively. Of the 19 animals that received a transplant of labeled SVZa cells, 13 animals were used for detailed analysis; the transplant was not placed in the striatumof the six brains (asterisk) excluded from further consideration.

Appearance of Cells at Injection Site

Three days after transplanting SVZa cells into P1 striatum BrdU-labeled SVZa cells were readily identified in the middle of the striatum and in some cases also along the injection tract running through the corpus callosum. The presence of labeled cells along the injection tract is probably due to the backflow of the cell suspension or because of a small amount of leakage of the labeled cells during insertion or withdrawal of the Hamilton syringe. The results show complete and heavy staining of the nuclei of the labeled cells soon after transplantation. Many of the BrdU-labeled cells were aggregated near blood vessels. In addition, at this short survival time cells were usually seen adjacent to each other, although a few cells were more dispersed within the striatum and had evidently undergone migration.

Patterns of Migration of Donor SVZa cells in the Host Striatum

Ordinarily at P0–P2 (the time when the SVZa cells were dissected for transplantation), the unmanipulated SVZa cells migrate several millimeters to the subependymal layer in the middle of the olfactory bulb. By 4 weeks they attain their final position in the granule cell or glomerular layers. The distribution of the labeled SVZa cells in the host striatum was therefore examined at 2 to 4 weeks after transplantation to investigate whether the SVZa cells had dispersed from their site of injection. Of the 19 animals, 15 animals which received SVZa transplants at the following range of coordinates A–P, 1.0–1.5 mm; M-L, 1.8–2.3 mm and depth, 2.5–3.5 mm were analyzed. Of the 15 animals injected, 2 animals did not show labeled cells in the striatum or along the striatal boundary. Instead, the BrdU-labeled cells were seen in the dorsal aspect of the corpus callosum indicating that the injection site was too superficial. Therefore the brains of the remaining 13 animals were analyzed. Three patterns of distribution of the transplanted SVZa cells were observed: (i) labeled cells were confined to the striatum; (ii) labeled cells were situated along the striatal boundary (between the striatum and the corpus callosum) and (iii) labeled cells were present in both of the above-mentioned locations. A striking finding of this study is that the injection site could not be demarcated 2–4 weeks post transplantation in any of the cases studied; nor were glial cells observed around the transplants. In addition, although SVZa cells were seen along the striatal boundary, they were never seen to cross it and migrate into the surrounding cerebral cortex.

Appearance and Distribution of SYZa Cells Restricted to Striatum.

The labeled SVZa cells were identified in the striatum in 5 out of 13 animals (Table 1) analyzed. In each brain the SVZa cells within the striatum occurred as individual cells or in small groups of usually no more than 2–4 cells. Large, closely packed aggregates of cells were never observed 2–4 weeks after transplantation, indicating that the cells had migrated away from each other. The labeled cells were frequently found in close proximity to blood vessels. Although the labeled cells were present through the striatum, in the majority of the brains analyzed the labeled SVZa cells were situated closer to the lateral ventricle than to the lateral edge of the striatum.

Amongst the transplanted cells labeled with PKH26, small clumps of 2–4 cells were seen extending processes into the striatum. The BrdU-labeled SVZa cells located in the striatum 2–4 weeks following transplantation were not heavily stained as cells examined 3 days post transplantation This suggested that the SVZa cells had undergone cell division after transplantation into the striatum. Our observations indicate that the heterotopically transplanted SVZa cells retained their capacity to concurrently divide and migrate.

Unlike other studies in which cells were transplanted into the striatum, glial cells were rarely seen associated with the transplants. The presence of glial cells, a sign that the host striatum is reacting to the local trauma produced by the implantation procedure, was absent in the SVZa transplants and could be attributed to the younger age of the donor and host animals used. The absence of the glial barrier could be partially responsible for the dispersion of the transplanted SVZa cells within the striatum. A possible reason the SVZa cells did not provoke an immune rejection by the host tissue could be because the SVZa cells used for transplantation were a substantially homogeneous population of neuronal progenitor cells. Neurons do not have antigen presenting capability and thus are not able to initiate an immune response. Glial cells, the early targets in a rejection process, are generally absent from the transplanted SVZa cell suspension.

Appearance and Distribution of SVZa Cells Restricted to the Striatal Boundary.

Even though similar coordinates were used for implantation in all the animals, the distribution of transplanted SVZa cells varied. In some cases (3 out of 15) following transplantation, the PKH26- or BrdU-labeled cells were identified only along the striatal boundary adjacent to the corpus callosum and not within the striatum proper (Table 1). Labeled SVZa cells were present along the dorsal, lateral and ventro-lateral aspects of the striatal boundary 2–4 weeks after implantation. The outlining of the contour of the striatum by labeled cells suggests that they had arrived at their position by migration, rather than being placed at the borders of the striatum simply as a result of the injection. Various intensities of BrdU staining was observed among the labeled SVZa cells, which were observed either individually or in small groups. The PKH26-labeled cells seen along the striatal boundary did not appear to have any prominent morphological features; they were often round without any processes similar to other individual cells. This indicates that the cells at the border of the striatum may not undergo differentiation as they do when situated in the striatum.

Appearance and Distribution of SVZa Cells within the Striatum and along the Striatal Boundary.

In 5 out of the 13 animals labeled cells were seen both within the striatum and along the striatal boundary (Table 1) 2–4 weeks following transplantation. Also various intensities of BrdU staining were observed amongst the labeled cells. In the majority of the cases the SVZa cells located within the striatum, were in closer proximity to the striatal boundary and labeled SVZa cells were distributed all along the striatal edge between the striatum and the corpus callosum as described previously.

The relationship of the Transplanted SVZa Cells to the Lateral Cortical Stream.

Of significance is the fact that in 8 of the 13 animals (62%) the SVZa cells were present along the striatal boundary. This region along the striatal boundary corresponds to the lateral cortical stream of migration described by Bayer and Altman in *Neocortical Development*, New York:Raven Press, Ltd., pp. 116–127 (1991) which is present prenatally and is used by ventricular zone-derived cells of the developing cortex to reach the lateral and ventro-lateral cortical plate. The presence of transplanted SVZa cells distributed along this curved pathway, suggests that the SVZa cells are able to decipher guidance cues, used by other migrating cells.

Example 9
Transfection of Neuronal Progenitor Cells

Cells were harvested from the SVZa, dissociated, and plated in 16 well chamber slides in Ham's F10 medium with 1% penicillin/streptomycin and 10% fetal calf serum. Between $3 \times 10^4$ and $8 \times 10^4$ cells per well were added. Either the next day or several hours later, the cells were infected with retrovirus (either BAG, which expresses βgal in the cytoplasm at $1.04 \times 10^6$ particles/ml, or nls-lacZ retroviral vector, which expresses βgal in the nucleus [gift of Dr. Gary Nolan; *Proc. Natl. Acad Sci. USA* 84:6795–6799 (1987)], at $1.54 \times 10^6$ particles/ml) in varying amounts (30 μl–200 μl) and 0.6 μl/well of a 1 mg/ml solution of polybrene was added. Cells were fixed a day later with 2% paraformaldehyde, 0.4% glutaraldehyde, 0.1 M PBS. The X-Gal incubation mixture (Luskin, *Neuron* 11:173 (1993)) was added and the number of blue cells/total cells in each dish was determined. Up to 4 % of the cells were blue, indicating they had been transfected or had inherited the transfected gene.

Example 10
Generation of Immortalized Clonal Cell lines from the SVZa

Primary cultures can be made at low density from dissociated SVZa from newborn rats. These cultures can then be transfection with a retrovirus containing both the temperature sensitive SV40 Large T and neo$^r$ genes. After the infection, G418 (a neomycin analog) can be added to the growth medium in order to select for cells that have integrated the retrovirus thus acquiring neomycin resistance. G418 selection can be maintained until colonies form on the dishes. After these colonies form, each can be isolated and expanded in separate dishes to produce sublines hopefully consisting of mitotic clones of a single infected primary cell.

Southern analysis can be used to verify or disprove the clonality of each subline. It is important to establish clonal cell lines due to the random nature of retroviral integration which may affect expression of the immortalizing Large T antigen. The SV40 Large T antigen cDNA can be used to probe several different restriction digests of genomic DNA isolated from each cell line. This can allow analysis of each subline for the length of the integrated construct, number of integration sites, and the clonal relationships between each line.

At the same time, each subline can be expanded in culture to demonstrate the ability to passage in vitro. As soon as enough cells are available, each subline can be frozen in order to preserve samples early in their immortalized life span.

To obtain cells from the SVZa, newborn (P0) Sprague-Dawley rat pups anesthetized by hypothermia can be decapitated, and the brains can be dissected into ice-cold $Ca^{2+}/Mg^{2+}$ free HBBS. After removal of meninges, the anterior portion of the subventricular zone can be dissected under the microscope (FIG. 1). This tissue can then be incubated in 0.15% trypsin in Eagle's Basal Medium for 20 minutes. Following this incubation, the tissue can undergo aspiration with a fire-polished Pasteur pipette to generate a single cell suspension. Cells can then be plated at a low density in 1:1 DMEM:HAMS media supplemented with 10% Fetal Bovine Serum and 1% Penicillin/Streptomycin onto several poly-D-lysine coated 35 mm plastic culture dishes. The cells can be grown at 39° C. for 24 hours.

Twenty-four hours after plating the primary SVZa cultures, the cells can be moved to 33° C., and the media can be replaced with the supernatant from the producer cell line containing the replication defective retrovirus encoding the ts SV40 Large T antigen. 8 μg/ml polybrene can also be added to the cultures to facilitate retroviral entry into the cells. After 4 hours, the retroviral supernatant can be replaced with fresh DMEM/HAMS medium, and the cells can be kept at 33° C. The following day, 0.5 mg/ml G418, a neomycin analog, can be added to the media in order to select for neomycin resistant cells. This selection media can be changed every 3–5 days. As colonies form on the dishes, they can be isolated with cloning rings and transferred to separate wells in a 24 well plate. Each subline can then be expanded and passaged to provide cells for study. A subset of each line can also be frozen in 10% DMSO in medium.

High molecular weight genomic DNA can be prepared from each cell line as previously described (Maniatis et al., *Molecular Cloning (A Laboratory Manual)*, Cold Spring Harbor, Cold Spring Laboratories, 1982). 10 μg of DNA can be cut with Xbal, EcoRI, and BgIII in separate reactions. Xbal cuts at both ends of the retroviral insert while both EcoRI and BgIII cut only once within the construct. Then, the DNA can be size fractionated on 0.8% agarose gels alongside DNA markers of known size and transferred to a nylon filter (GeneScreen Plus, Dupont) as described by Southern, 1975. The filterbound DNA can then be hybridized to a random primed SV40 Large T antigen probe under stringent conditions.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. An isolated cellular composition comprising greater than 90% mammalian, non-tumor derived, neuronal progenitor cells which, while capable of cell division, express a neuron-specific marker and which give rise to progeny which differentiate into neuronal cells.

2. The composition of claim 1, wherein greater than 95% of the mammalian, non-tumor derived neuronal progenitor cells express a neuronal marker and give rise to progeny which differentiate into neuronal cells.

3. The composition of claim 1, wherein the isolated neuronal progenitor cells, without being first immortalized, divide for at least two generations.

4. The composition of claim 1, wherein the neuronal progenitor cells are rat cells.

5. The composition of claim 1, wherein the neuronal progenitor cells are human cells.

6. The composition of claim 1, wherein at least a portion of the population of neuronal progenitor cells, or their progeny, is transfected with an exogenous nucleic acid.

7. The composition of claim 6, wherein the exogenous nucleic acid functionally encodes a biologically active molecule.

8. The composition of claim 7, wherein the exogenous nucleic acid functionally encodes a biologically active molecule that stimulates cell division or differentiation.

9. The composition of claim 7, wherein the exogenous nucleic acid functionally encodes a biologically active molecule that functions in the synthesis of a neurotransmitter.

10. A method of obtaining an isolated cellular composition comprising greater than 90% mammalian, non-tumor derived, neuronal progenitor cells which express a neuronal marker and which give rise to progeny which differentiate into neuronal cells, comprising isolating cells from the portion of a mammalian brain that is the equivalent of the anterior portion of the subventricular zone at the dorsolateral portion of the anterior-most extent of the region surrounding the ventricle of a neonatal rat brain.

11. An isolated cellular composition comprising greater than 50% mammalian, non-tumor derived, neuronal progenitor cells which express a neuron-specific marker and which give rise to progeny which differentiate into neuronal cells.

12. An isolated cellular composition of mammalian, non-tumor derived, neuronal progenitor cells prepared by the method of claim 10.

13. The isolated cellular composition of neuronal progenitor cells of claim 12, wherein said mammalian, non-tumor derived, neuronal progenitor cells divide for at least two generations without being first immortalized.

14. The isolated cellular composition of neuronal progenitor cells of claim 12, wherein said mammalian, non-tumor derived, neuronal progenitor cells are rat cells.

15. The isolated cellular composition of neuronal progenitor cells of claim 12, wherein said mammalian, non-tumor derived, neuronal progenitor cells are human cells.

16. The isolated cellular composition of neuronal progenitor cells of claim 12, wherein greater than 95% of the mammalian, non-tumor derived, neuronal progenitor cells express a neuronal marker and give rise to progeny which differentiate into neuronal cells.

* * * * *